United States Patent
Pasini et al.

(10) Patent No.: US 9,492,296 B2
(45) Date of Patent: Nov. 15, 2016

(54) STENT DEVICES MADE OF A LATTICE WITH SMOOTH SHAPE CELLS IMPROVING STENT FATIGUE LIFE

(71) Applicant: THE ROYAL INSTITUTION FOR THE ADVANCEMENT OF LEARNING / MCGILL UNIVERSITY, Montreal (CA)

(72) Inventors: Damiano Pasini, Montreal (CA); Ehsan Masoumi Khalil Abad, Longueuil (CA)

(73) Assignee: THE ROYAL INSTITUTION FOR THE ADVANCEMENT OF LEARNING/MCGILL UNIVERSITY, Montreal (CA)

(*) Notice: Subject to any disclaimer, the term of this patent is extended or adjusted under 35 U.S.C. 154(b) by 224 days.

(21) Appl. No.: 13/659,398

(22) Filed: Oct. 24, 2012

(65) Prior Publication Data

US 2014/0114430 A1    Apr. 24, 2014

Related U.S. Application Data

(60) Provisional application No. 61/551,096, filed on Oct. 25, 2011.

(51) Int. Cl.
*A61F 2/915* (2013.01)
*G06F 17/50* (2006.01)
*A61F 2/86* (2013.01)
(Continued)

(52) U.S. Cl.
CPC .............. *A61F 2/915* (2013.01); *G06F 17/50* (2013.01); *A61F 2/07* (2013.01); *A61F 2/2418* (2013.01); *A61F 2/86* (2013.01);
(Continued)

(58) Field of Classification Search
None
See application file for complete search history.

(56) References Cited

U.S. PATENT DOCUMENTS 5,636,338 A * 6/1997 Moreton ...................... 345/442
5,928,246 A   7/1999 Gordon et al.
(Continued)

FOREIGN PATENT DOCUMENTS

WO    2004049973    6/2004

OTHER PUBLICATIONS

Teng et al., "Shape Synthesis in Mechanical Design," Acta Polytechnica, vol. 47, No. 6, pp. 56-62, 2008.*
(Continued)

*Primary Examiner* — Kibrom K Gebresilassie
(74) *Attorney, Agent, or Firm* — Norton Rose Fulbright Canada LLP

(57) ABSTRACT

A method for generating a lattice cell shape for a stent comprising generating a unit cell model representing a stent cell to be made of a given material, the unit cell model comprising elements each comprising points defining a $G^2$-continuous curve, setting a weighting factor to a same value for each one of the points, the weighting factor representing a contribution of a corresponding one of the points to a curvature of an optimal curve, determining a curvature of the $G^2$-continuous curve as a function of the weighting factors having the same value, and structurally optimizing the unit cell model by iteratively determining a variable value for the weighting factor value using stress-strain characteristics for the given material, determining a new curvature of the $G^2$-continuous curve as a function of the variable value, and minimizing the new curvature, thereby obtaining an optimized curve corresponding to an optimized lattice cell shape.

22 Claims, 13 Drawing Sheets

(51) Int. Cl.
*A61F 2/07* (2013.01)
*A61F 2/24* (2006.01)

(52) U.S. Cl.
CPC ............... *A61F 2002/91575* (2013.01); *A61F 2230/0013* (2013.01); *A61F 2230/0054* (2013.01)

(56) References Cited

U.S. PATENT DOCUMENTS

| | | | |
|---|---|---|---|
| 7,735,449 B1 | 6/2010 | Harold et al. | |
| 2001/0044652 A1* | 11/2001 | Moore ..................... | 623/1.16 |
| 2004/0225346 A1* | 11/2004 | Mazumder et al. ......... | 623/1.13 |
| 2005/0096733 A1* | 5/2005 | Kovneristy et al. ......... | 623/1.22 |
| 2006/0136037 A1* | 6/2006 | DeBeer et al. ............. | 623/1.15 |
| 2006/0264810 A1 | 11/2006 | Hattler et al. | |
| 2008/0188924 A1* | 8/2008 | Prabhu ..................... | A61F 2/82 623/1.16 |
| 2008/0221666 A1* | 9/2008 | Licata et al. ................ | 623/1.22 |
| 2009/0099644 A1* | 4/2009 | Biadillah et al. ............ | 623/1.16 |
| 2010/0049300 A1* | 2/2010 | Harder ...................... | 623/1.15 |
| 2011/0276123 A1* | 11/2011 | Davies ..................... | A61F 2/88 623/1.15 |
| 2012/0214384 A1* | 8/2012 | Harder ...................... | 451/36 |
| 2012/0303112 A1* | 11/2012 | Armstrong ............... | A61F 2/07 623/1.16 |

OTHER PUBLICATIONS

B. B Barsky and T. DeRose, "Geometric Continuity of Parametric Curves," Berkely Computer Graphics Laboratory, Computer Science Division, Dept. of EE and CS, University of California, Berkely, Technical Report No. UCB/CSD 84/205, Oct. 1984.*
C. P. Teng, S. Bai, J. Angeles, "Shape Synthesis in Mechanical Design", pp. 1-10, 2008.*
D. Stoeckel, C. Bonsignore and S. Duda, A Survey of Stent Designs, NDC, Min Invas Ther & Allied Technol 11 (4), pp. 137-147, 2002, Fremont, California, USA.

* cited by examiner

000

STENT DEVICES MADE OF A LATTICE WITH SMOOTH SHAPE CELLS IMPROVING STENT FATIGUE LIFE

CROSS-REFERENCE TO RELATED APPLICATIONS

This application claims priority under 35 USC §119(e) of U.S. Provisional Patent Application No. 61/551,096 filed on Oct. 25, 2011, the contents of which are incorporated herein by reference.

TECHNICAL FIELD

The present invention relates to the field of medical stents, and more particularly to methods and systems for designing medical stents, and the stents produced thereby.

BACKGROUND

Intravascular stents are primarily used to open and scaffold tubular passages or lumens such as blood vessels, biliary ducts and the esophagus. They usually consist of expandable lattice meshes that can deploy and hold endovascular grafts, arterial endoprosthesis and self-expanding heart valve implants.

An increasing demand for endovascular stents has lead to significant advancements in the field of analysis, modeling and design. Despite intense research on the subject, some challenges have not yet been fully addressed. For example, over a ten year period of expected lifespan, a stent may undergo nearly four hundred million load cycles, arising mainly from pulsating blood pressure and body movement. Such a cyclic loading drastically amplifies the effect of stress concentration, which may severely reduce the fatigue life of the stent and may eventually lead to fatigue failure.

Peak stresses due to stress concentrations tend to occur in the lattice structures of known prior art stents, which lead to fatigue life issues and other undesirable characteristics. More particularly, lattices formed of closed cells having uneven shapes or curved boundaries having abrupt changes in geometry will tend to cause undesirable stress concentrations. Peak stresses due to stress concentration are also a crucial factor in the delamination of a polymer coating from an arched region of a lattice stent. This phenomenon has the potential to contribute to thrombus formation and can lead to in-stent restenosis and/or change of drug release rate for drug eluted stents.

Therefore, there is a need for an improved stent design.

SUMMARY

In accordance with a first aspect, there is provided a method for generating a lattice cell shape for a stent made of a lattice of a given material comprising: generating a unit cell model representing the lattice cell, the unit cell model comprising a plurality of geometric primitives interconnected by blending points, each of the geometric primitives defining a G2-continuous curve at the blending points; setting a weighting factor to a same value for each one of the plurality of blending points, the weighting factor representing a contribution of a corresponding one of the plurality of blending points to a curvature of an optimal curve; determining a curvature of the $G^2$-continuous curve as a function of the weighting factors having the same value; and structurally optimizing the unit cell model by iteratively determining a variable value for the weighting factor value for each one of the plurality of blending points using stress and/or strain characteristics for the given material, determining a new curvature of the $G^2$-continuous curve as a function of the variable value, and minimizing said new curvature, thereby obtaining an optimized curve corresponding to an optimized shape of the lattice cell.

In accordance with a second broad aspect, there is provided a method of forming a stent of a given material with a lattice structure having a plurality of lattice cells, the method comprising: generating a unit cell model representing one of said lattice cells, the unit cell model comprising a plurality of geometric primitives each having a plurality of blending points interconnecting the geometric primitives and defining a $G^2$-continuous curve; setting a weighting factor to a same value for each one of the plurality of blending points, the weighting factor representing a contribution of a corresponding one of the plurality of blending points to a curvature of an optimal curve; determining a curvature of the $G^2$-continuous curve as a function of the weighting factors having the same value; structurally optimizing the unit cell model by iteratively determining a variable value for the weighting factor value for each one of the plurality of blending points using stress and/or strain characteristics for the given material, determining a new curvature of the $G^2$-continuous curve as a function of the variable value, and minimizing the new curvature, thereby obtaining an optimized curve corresponding to an optimized lattice cell shape; forming a 2D lattice structure of the given material by replicating the optimized lattice cell shape to form the lattice structure having a plurality of the lattice cells; and folding the lattice structure to form a tubular 3D lattice, thereby creating the stent.

In accordance with another broad aspect, there is provided a stent comprising a lattice structure having a substantially tubular shape, the lattice structure comprising a plurality of replicated lattice cells having a lattice cell shape as described with respect to the associated method of forming such lattice cell shapes.

In accordance with another broad aspect, there is provided a system for generating a lattice cell shape for a stent comprising: a unit cell generator for generating a unit cell model representing a stent cell to be made of a given material, the unit cell model comprising a plurality of geometric primitives each comprising a plurality of blending points defining a $G^2$-continuous curve; and a structural optimization module for iteratively determining a variable value for a weighting coefficient for each one of the plurality of blending points using stress and/or strain characteristics for the given material, the weighting coefficient representing a contribution of a corresponding one of the plurality of blending points to a curvature of an optimal curve, determining a curvature of the $G^2$-continuous curve as a function of the variable value, and minimizing the curvature in order to obtain an optimized curve corresponding to an optimized stent cell shape.

In accordance with a further broad aspect, there is provided a system for forming a stent lattice structure for a stent comprising: a unit cell generator for generating a unit cell model representing a stent cell to be made of a given material, the unit cell model comprising a plurality of geometric primitives each comprising a plurality of blending points defining a $G^2$-continuous curve; a geometry optimization module for setting a weighting coefficient to a same value for each one of the plurality of blending points, the weighting factor representing a contribution of a corresponding one of the plurality of blending points to a curvature of an optimal curve, determining a curvature of the $G^2$-continuous curve as a function of the weighting factors having the same value, and optimizing a geometry of the unit cell model by minimizing the curvature of the $G^2$-continuous curve in order to obtain an intermediate curve representing an intermediate unit cell model; a structural optimization module for iteratively determining a variable value for the weighting factor value for each one of the plurality of blending points using stress and/or strain characteristics for the given material, determining a curvature of the intermediate curve as a function of the variable value, and minimizing the curvature in order to obtain an optimized curve corresponding to an optimized stent cell shape; and a stent generator which replicates the optimized stent cell shape and forms a stent lattice structure.

In accordance with still another broad aspect, there is provided a computer readable memory having stored thereon: program code of a unit cell generator executable by a processor to generate a unit cell model representing a stent cell to be made of a given material, the unit cell model comprising a plurality of geometric primitives each comprising a plurality of blending points defining a $G^2$-continuous curve; program code of a geometry optimization unit executable by the processor to set a weighting coefficient to a same value for each one of the plurality of blending points, the weighting factor representing a contribution of a corresponding one of the plurality of blending points to a curvature of an optimal curve, determine a curvature of the $G^2$-continuous curve as a function of the weighting factors having the same value, and minimize the curvature of the $G^2$-continuous curve, thereby obtaining an intermediate curve representing an intermediate unit cell model; and program code of a structure optimization unit executable by the processor to iteratively determine a variable value for the weighting factor value for each one of the plurality of blending points using stress and/or strain characteristics for the given material, determine a curvature of the intermediate curve as a function of the variable value, and minimize the curvature, thereby obtaining an optimized curve corresponding to an optimized stent cell shape.

BRIEF DESCRIPTION OF THE DRAWINGS

Reference will now be made to the accompanying drawings.

It will be noted that throughout the appended drawings, like features are identified by like reference numerals.

DETAILED DESCRIPTION

Based on the mechanism of deployment, stents can be classified into balloon expanding (BE) or self expanding (SE). BE stents, which are manufactured in the form of a tube with a radius smaller than the target vessel, are deployed using a retractable inflatable balloon. After the balloon deflates and retracts, the stent structure plastically deforms and preserves its deployed shape. In contrast, SE structures are manufactured from tubes with a diameter larger than that of the target vessel. For delivery and insertion purposes, the structure is compressed elastically into the smaller diameter of the delivery catheter, which is then inserted percutaneously into the body. Upon reaching the desired position, the casing sheath is removed and the stent elastically deploys to its original shape.

FIGS. 1a-1f illustrate some prior art stent devices which are designed to deploy into a body by minimally invasive percutaneous intervention, namely a self-expanding CoreValve™ stent device, a Symetis™ W aortic stent valve, a Viatorr™ stent-graft, a Wallstent™ Cobalt SE stent, a SMART™ Nitinol SE stent, and a diamond-cell stent.

Figure 1:
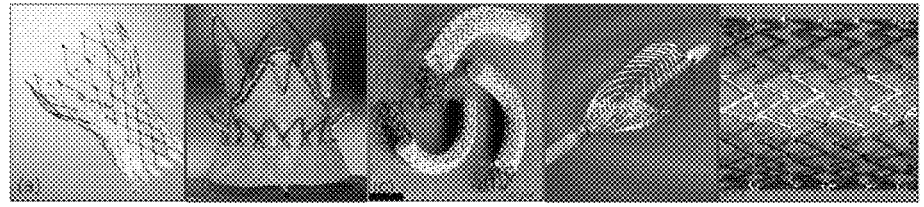
FIGS. 1a-1f illustrate stent devices according to the prior art.
Figure 1:
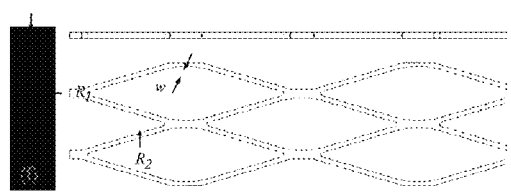

The impact of the design and optimization of these prior art stent has received minor attention. For example, FIG. 1f illustrates the structural geometry of a diamond-cell stent with closed lattice cells. Each lattice cell has an uneven shape, the boundaries curves having abrupt changes in geometry. This curvature discontinuity at the blending points between the arc geometric primitives of the stent and the linear segments generate stress concentration that may increase significantly the level of stress.

Shape, size, topology and thickness of a stent lattice cell are geometric variables that may be tailored to improve fatigue life and mechanical performance of stent structures, either BE or SE.

In the following, there is provided a design method for the shape synthesis of smooth cell geometry that can yield a lattice stent having reduced stress concentration, thereby reducing its risk of fatigue failure, and a stent lattice structure produced by such a design method. There is first presented a design strategy to synthesize the cell shape of a two-dimensional lattice for SE stents. Results obtained by the application of the design method are compared with the characteristics of an existing Nitinol SE graft commonly used in abdominal aortic aneurisms repair. Furthermore, through a parametric study of the optimized lattice stents, the effect of selected geometric parameters, e.g. tube thickness, strut width, and number of lattice cells, on stent fatigue life are presented.

Over an expected life-span of 10 years, stents may undergo nearly $4 \times 10^8$ cycles of alternating forces arising from pulsating blood pressure and body movement. Such a loading condition could potentially lead to fatigue failure, especially for stents made of Nitinol, which has a lower resistance to fatigue crack growth in comparison to other metals.

Stress concentration is triggered by the presence of a curvature discontinuity at the blending points between the geometric primitives which define the cell shape. The presence of such a curvature discontinuity in a mechanical component may cause drastic rise of the stress level, which in turn harshly harms its fatigue life. Referring back to FIG. 1f, the mesh structure of the stent exhibits a non-smooth shape characterized by sharp corners, which increases the stress regime at those blending points, thereby accelerating its fatigue failure. To remove geometry discontinuity in a stent, there is herein proposed a method to synthesize the unit cell of the stent lattice with curves that are continuous in their curvature, i.e. the boundaries shaping each lattice cell are $G^2$-continuous, in a manner similar to that described by Teng et al. in "Shape Synthesis in Mechanical Design" (Teng et al., Acta Polytechnica, Vol. 47, No. 6, pp. 56-62, 2008), the entire content of which is incorporated herein by reference.

Through the formulation of a structural optimization problem described below, it is first imposed that each of the cell members be $G^2$-continuous at the blending points between the geometric primitives defining a cell as well as at the points interconnecting adjacent cells, and then be as straight as possible, i.e. with the smallest possible curvature, to avoid high bending moments caused by curved cell members.

Figure 2:
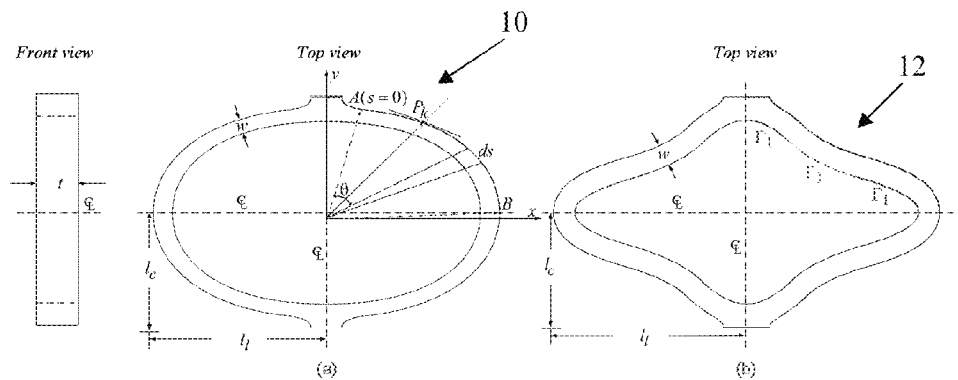
FIGS. 2a and 2b illustrate an E stent lattice cell and a D stent lattice cell, respectively, in accordance with an embodiment.

FIG. 2 illustrates two possible examples of unit cells 10 and 12 of a stent lattice cell having a shape which is formed by curves that are continuous in their curvature and therefore which have boundaries that are $G^2$-continuous. While these two shapes are depicted, other shaped cells which adhere to the presently described method and system for determining the shape of the lattice cells are also possible. For example, a diamond shaped lattice cell having rounded corners may also be determined and formed as described herein. The lattice cells of FIG. 2 are formed of a number of geometric primitives which are connected by blending points, the cells being $G^2$-continuous at the blending points between the geometric primitives as well as at the points interconnecting adjacent cells. Each of the geometric primitives therefore begin with a common radius of curvature, and are then optimized as described herein in order to minimize the curvature as much as possible by making them as straight as possible (i.e. with the smallest possible curvature). The unit cell 10, 12 is replicated along two directions in a planar sheet to form a stent lattice, which is then folded into a cylindrical 3D surface forming a lattice cylinder. The lattice cylinder is described by $n_c$ cells in the circumferential direction and $n_l$ cell rows in the longitudinal direction. The tube thickness and strut width are respectively t and w. Due to similarity with the diamond and super-ellipse shapes, the cell topologies 10 and 12 illustrated in FIG. 2 are referred to as "D cell" and "E cell" hereinafter, respectively.

Figure 3:
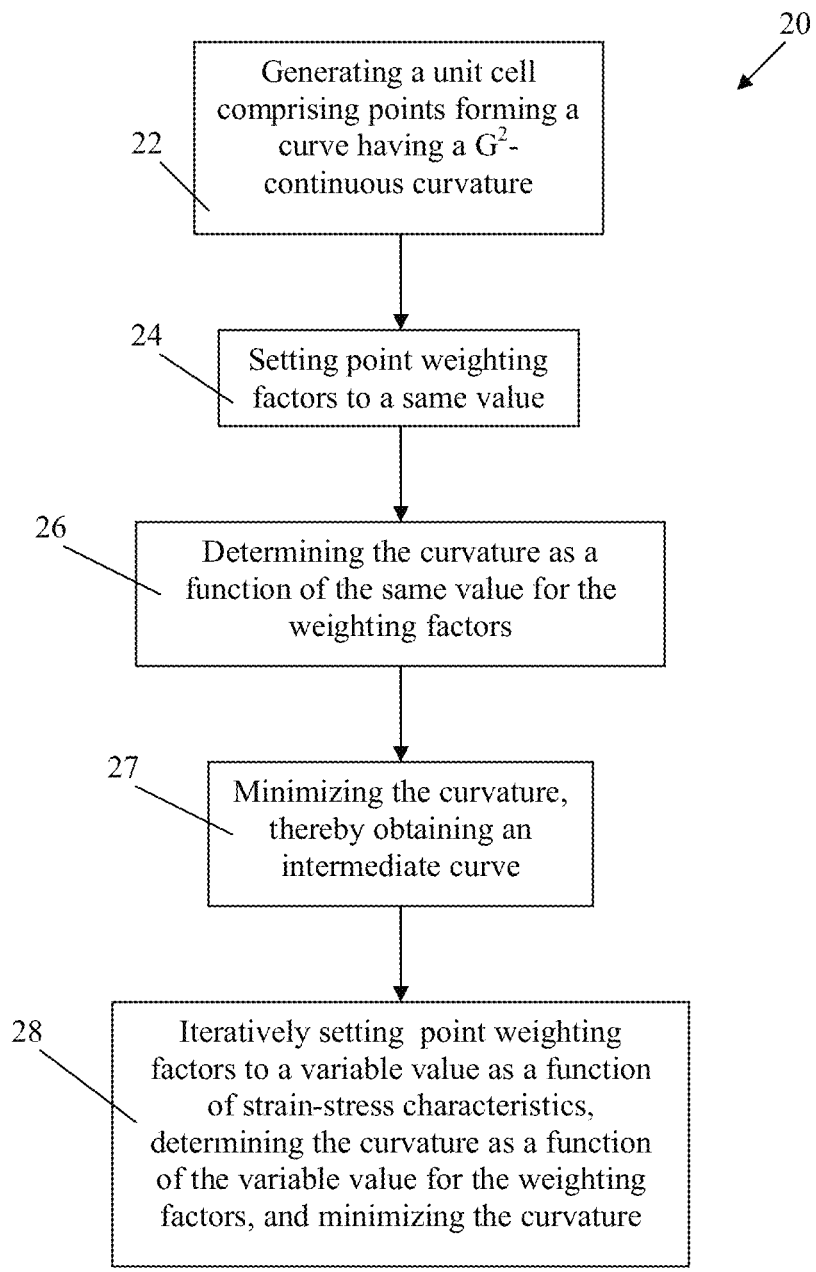
FIG. 3 is a flow chart illustrating a method for designing a stent cell, in accordance with an embodiment.

FIG. 3 illustrates one embodiment of a design method 20 for optimizing the shape of a stent lattice cell. The design method is based on the synthesis of structural members with $G^2$-continuous curves that minimize the root mean square of the cell curvature. The first step 22 consists in generating a unit cell model representing a stent cell and having a substantially $G^2$-continuous curvature. At step 24, a weighting coefficient representing a contribution of the blending points to the curvature of an optimal curve is set to a same value for each point. At step 26, the curvature is expressed as a function of the weighting factors having the same value. At step 27, a geometry optimization is performed, i.e. the curvature is minimized. The geometry optimization consists in minimizing only the root mean square (rms) value of the curvature of the cell geometric primitives. At steps 24, 26, and 27, the material properties and pseudo-elastic behavior of Nitinol are ignored. At step 28, a structure optimization of the unit cell using the attributes and stress-strain curve of the stent material to be factored is performed. The structure optimization consists in iteratively determining a variable value for the weighting factor value for the blending points using stress and/or strain characteristics for the stent material, expressing the curvature as a function of the variable values, and minimizing the curvature. While a strain-based weighting factor was used in at least one embodiment of the presently disclosed method, and more particularly given the selection of Nitirol as the material of the lattice in the embodiment in question, it is also possible to use a stress-based weighting factor.

Referring to FIG. 2, the shape synthesis of the lattice strut is stated as follows: under given end conditions, find a boundary-curve $\Gamma$ that connects two given end blending points A and B of the cell strut as smoothly as possible and with a $G^2$-continuous curve. By parametrizing the cell strut boundary-curve $\Gamma$ as a function of the arc-length along the strut, the optimization problem may be formulated as:

$$J(\Gamma) = \frac{1}{L}\int_A^B \kappa^2 ds \to \min_{\Gamma(s)} \qquad (1)$$

where $\sqrt{J}$ is the rms value of the curvature, k, of a cell member boundary-curve, L is the member length, A and B are its end-blending points, and ds is the arc-length along the member, starting from 0 at point A, as shown in FIG. 2. The member boundary-curve is subjected to four constraints at each end-point: two constrain the end-blending points of each curve of the lattice cell, while the other set the tangent and curvature of the curve at these blending points.

Equation 1 can be treated as a problem of mathematical programming by means of non-parametric cubic splines. Hence, each boundary curve is discretized by n+2 supporting blending points $\{P_k\}_0^{n+1}$ that are defined by $P_k(\rho_k,\theta_k)$ in a polar coordinate system.

As illustrated in FIG. 2, $P_k$ is a generic point of the curve; $P_0 = A$ and $P_{n+1} = B$, where $A(\rho_A,\theta_A)$, and $B(\rho_B,\theta_B)$ are two end-blending points of the boundary-curve of each cell element. Moreover, if it is assumed that the discrete blending points are located at constant tangential intervals, the tangential increment is:

$$\Delta\theta = \frac{\theta_B - \theta_A}{n+1} \quad (2)$$

A cubic spline, $\rho(\theta)$, between two consecutive supporting blending points Pk and $P_{k+1}$ can be defined as:

$$\rho(\theta) = A_k(\theta - \theta_k)^3 + B_k(\theta - \theta_k)^2 + C_k(\theta - \theta_k)^2 + D_k \quad (3)$$

The radial coordinates, the first and second derivatives of the cubic splines at the $k^{th}$ supporting point, $\rho$, $\rho'$, and $\rho''$, respectively, are represented by the following three vectors:

$$\rho = [\rho_0, \rho_1, \ldots \rho_n, \rho_{n+1}]^T$$

$$\rho' = [\rho'_0, \rho'_1, \ldots \rho'_n, \rho'_{n+1}]^T$$

$$\rho'' = [\rho''_0, \rho''_1, \ldots \rho''_n, \rho''_{n+1}]^T \quad (4)$$

Imposing the $G^2$-continuity condition results in the following linear relationships between $\rho$ and $\rho''$, and between $\rho$ and $\rho'$:

$$A\rho'' = 6C\rho \text{ and } P\rho' = Q\rho \quad (5)$$

where A, C, P, and Q are defined as follows.

$$A = \Delta\theta \begin{bmatrix} 2 & 1 & 0 & 0 & \ldots & 0 & 0 \\ 1 & 4 & 1 & 0 & \ldots & 0 & 0 \\ 0 & 1 & 4 & 1 & \ldots & 0 & 0 \\ \vdots & \vdots & \vdots & \vdots & \ldots & \vdots & \vdots \\ \vdots & \vdots & \vdots & \vdots & \ldots & \vdots & \vdots \\ 0 & 0 & \ldots & 1 & 4 & 1 & 0 \\ 0 & 0 & 0 & \ldots & 1 & 4 & 1 \\ 0 & 0 & 0 & \ldots & 0 & 1 & 2 \end{bmatrix}$$

$$C = \frac{1}{\Delta\theta} \begin{bmatrix} c_{11} & 1 & 0 & 0 & \ldots & 0 & 0 \\ 1 & -2 & 1 & 0 & \ldots & 0 & 0 \\ 0 & 1 & -2 & 1 & \ldots & 0 & 0 \\ \vdots & \vdots & \vdots & \vdots & \ldots & \vdots & \vdots \\ \vdots & \vdots & \vdots & \vdots & \ldots & \vdots & \vdots \\ 0 & 0 & \ldots & 1 & -2 & 1 & 0 \\ 0 & 0 & 0 & \ldots & 1 & -2 & 1 \\ 0 & 0 & 0 & \ldots & 0 & 1 & c_{n''n''} \end{bmatrix}$$

where $$n'' = n + 2;$$

$$c_{11} = -1 - \frac{\Delta\theta}{t_A}$$

and $$c_{n''n''} = -1 - \frac{\Delta\theta}{t_B}$$

$$P = \Delta\theta \begin{bmatrix} 1/\Delta\theta & 0 & 0 & 0 & \ldots & 0 & 0 \\ 1 & 4 & 1 & 0 & \ldots & 0 & 0 \\ 0 & 1 & 4 & 1 & \ldots & 0 & 0 \\ \vdots & \vdots & \vdots & \vdots & \ldots & \vdots & \vdots \\ \vdots & \vdots & \vdots & \vdots & \ldots & \vdots & \vdots \\ 0 & 0 & \ldots & 1 & 4 & 1 & 0 \\ 0 & 0 & 0 & \ldots & 1 & 4 & 1 \\ 0 & 0 & 0 & \ldots & 0 & 0 & 1/\Delta\theta \end{bmatrix}$$

$$Q = \frac{1}{\Delta\theta} \begin{bmatrix} 1/t_A & 0 & 0 & 0 & \ldots & 0 & 0 \\ -3 & 0 & 3 & 0 & \ldots & 0 & 0 \\ 0 & -3 & 0 & 3 & \ldots & 0 & 0 \\ \vdots & \vdots & \vdots & \vdots & \ldots & \vdots & \vdots \\ \vdots & \vdots & \vdots & \vdots & \ldots & \vdots & \vdots \\ 0 & 0 & \ldots & -3 & 0 & 3 & 0 \\ 0 & 0 & 0 & \ldots & -3 & 0 & 3 \\ 0 & 0 & 0 & \ldots & 0 & 0 & 1/t_B \end{bmatrix}$$

With $t_A = \tan\gamma_A$ and $t_B = \tan\gamma_B$, where $\gamma_A$ and $\gamma_B$ are the tangent angles made by the tangent to the curve with the radius vector at the end-points A and B, as shown in FIG. 2. Furthermore, $\rho_0 = \rho_A$ and $\rho_{n+1} = \rho_B$ are known from a given parameter vector of the cell. Now, if x is the vector of the design variables, defined as $$x = [\rho_1, \ldots \rho_n]^T \quad (6).$$

In the discretized shape optimization problem, equation 1 can be written as:

$$z(x) = \frac{1}{n}\sum_1^n w_k \kappa_k^2 \to \frac{\min}{x} \quad (7)$$

where $w_k$ is the weighting coefficient of point $k^{th}$ defined at each supporting point, and representing the contribution of each point to the curvature of the optimum curve. Z(x) therefore represents the discretization of the functional equation given in Equation 1. Furthermore, the curvature at each point $P_k$ is given by:

$$\kappa_k = \frac{\rho_k^2 + 2(\rho'_k)^2 - \rho_k \rho''_k}{(\rho_k^2 + (\rho'_k)^2)^{3/2}} \quad (8)$$

Discretizing the objective function, i.e. equation 7, and applying the constraints at the end blending points of the boundary curve, allows the problem to be solved with mathematical programming. A sequential-quadratic-programming algorithm using orthogonal decomposition is implemented to solve this problem, although other algorithms may also be used.

As previously stated, the step 24 of geometry optimization assumes equal weighting coefficients, i.e. 1/n to find a geometrically optimum boundary of the unit cell, whereby several iterations may be performed as part of the design optimization in order to find the minimum curvature desired. This result is then further optimized at step 26, in which the stress and strain regimes are taken into account. In this case, the expressions of the weighting coefficients, $w_k$, (see equation 7) are considered as a function of the strain regime obtained iteratively at each finite element analysis (FEA) iteration.

While geometric optimization is performed above in the given example of the presently described method, the process of going through the geometric optimization problem is in fact not necessary. While curvature minimization is critical to the present process, it is nonetheless possible not to perform any geometric optimization and to perform only the structural optimization step.

Figure 4:
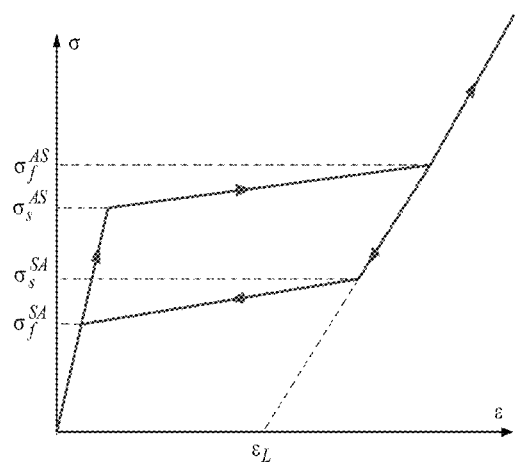
FIG. 4 schematic illustrates an exemplary stress-strain curve of Nitinol at a given temperature.

In an embodiment where the stent is to be made of Nitinol, strain is considered rather than stress, since the plateau region of the Nitinol stress-strain curve is much more sensitive to strain changes, as illustrated in FIG. 4. The weight coefficients are therefore not uniform along the cell strut boundary-curve and they are defined as:

$$w_k = \frac{\bar{\varepsilon}_k}{\bar{\varepsilon}_T} \quad (9)$$

where $\bar{\varepsilon}_k$ and $\bar{\varepsilon}_T$ are, respectively, the rms value of the von Mises strain at the $k^{th}$ supporting point of the profile curve, and the rms value of the strain over the whole cell element of the stent and are defined as:

$$\bar{\varepsilon}_T = \sqrt{\frac{1}{m}\sum_{i=1}^{m}\varepsilon_i^2} \quad (10)$$

$$\bar{\varepsilon}_k = \sqrt{\frac{1}{\mu_k}\sum_{i=1}^{\mu_k}\varepsilon_{ki}^2}, \quad (11)$$

$$\mu_k = \frac{m}{50}$$

where m is the total number of nodes in the FE model, $\varepsilon_i$ is the von Mises strain at $i^{th}$ node and $\varepsilon_{ki}$ is the von Mises strain of the $\mu_k$ nodes (2% of the total nodes of FE model for example), which are relatively closer to the $k^{th}$ supporting point. The structural optimization algorithm is set to end when the reduction in the maximum strain value is smaller than a predetermined value such as 0.1% for example.

The skilled person will understand that the stent may be made from materials other than Nitinol. For example, the stent may be formed of 316L stainless steel, cobalt-chromium-nickel-molybdenum, iron alloy, tantalum, or a plastic such as polyethylene or polyurethane. The choice of material for the stent will depend on the application and intended use of the stent. For each of these materials, the stress-strain characteristics will differ. While in the present example where the material selected is Nitinol, weight factors were calculated based on strain because Nitinol is much more sensitive to strain in the plateau region as seen in FIG. 4. With other materials, however, the weight coefficient, as shown in Equations 9 and 10 above, can alternately be calculated through stresses instead.

In one embodiment, the above described method for generating a stent cell shape may be converted to a method for generating a shape for the stent by performing two further steps consisting in replicating the unit cell obtained via the method 20 to form a stent lattice, and folding the stent lattice to form a substantially cylindrical 3D surface which corresponds to the desired stent structure.

The following presents an application of the above described method to the design of stents with smooth lattice geometry. Nitinol stent grafts have been successfully and widely employed in endovascular repair for abdominal aortic aneurisms (AAAs). The success of aneurism repairs, however, is often undermined by issues entailing stent-graft fatigue, graft migration, and blood leakage into the aneurysm cavity. It has been shown that two strategies may be adopted to reduce these risks. The first one is to stiffen the stent in the radial direction, thereby reducing the risk of endovascular leakage and device migration. The second one is to reduce the level of the alternating strain generated by a pulsating blood pressure with the objective of lowering the risk of fatigue failure.

In the following, the design method 20 is applied to optimize both the radial stiffness and fatigue life of a stent. The obtained stent is compared to a benchmark stent design by assuming a stent total length of 100 mm and a non-shrunk diameter of 30 mm. The risk of fatigue failure is expressed by a fatigue safety factor, obtained by dividing the 0.4% Nitinol endurance limit by the maximum alternating strain of the stent. Furthermore, the sensitivity of the radial stiffness and fatigue safety factor to the change of selected parameters defining stent geometry is studied.

ANSYS™ finite element modeling (FEM) software was used to analyze the radial size reduction occurring during the delivery process of the stent and the contact between the stent and the arterial wall after stent-graft deployment. In this study, only the stent rows in contact with the aneurism neck were examined due to their importance for stent-graft migration and fatigue life. The study, however, can be extended to the main body of the stent-graft by considering the contact between the whole stent and the graft. The 2D stent geometry was automatically synthesized through an in-house Matlab™ subroutine, which is coupled with ANSYS™ to build, mesh, and solve the 3D model of the stent. Because of symmetry in both geometry and loading, only ¼ of one cell was modeled. Symmetric boundary conditions were applied at the planes of symmetry. To mesh the stent geometric primitives of the lattice cell, a 3D eight-node element type, i.e. SOLID 185 of ANSYS™, was selected. The arterial wall was modeled as a cylinder and meshed by a twenty-node element type, i.e. SOLID 95 of ANSYS™. A mesh sensitivity test was performed to ensure the independency of the results from the mesh size.

Nitinol is a pseudo-elastic material extensively used in biomedical devices for its bio-compatibility, shape memory property besides outstanding ability to withstand severe deformation. FIG. 4 illustrates a schematic view of the stress-strain curve of Nitinol at a given temperature. To model the super-elastic characteristics of Nitinol, a constitutive model presented by Auricchio F (1995), "Shape Memory Alloys: Applications, Micromechanics, Macromodeling and Numerical Simulations", University of California at Berkely, was used. The following material attributes were assumed:

$\sigma_s^{AS}$=600 MPa, $\sigma_f^{AS}$=670 MPa, $\sigma_s^{SA}$=288 MPa, $\sigma_f^{SA}$=254 MPa, $\varepsilon_L$=6.3%, $E_A$=51.7 GPa, $E_M$=47.8 GPa, v=0.3 where E is the Young's modulus and v is the Poisson ratio while the indices A and M refer to the austenite and martensite phases.

The structure of the artery wall is assumed to be incompressible with a Young's modulus of 1.2 MPa and a Poisson's ratio of 0.495, as prescribed by FDA protocols (ASTM 2007).

The loading conditions include shrinking loading conditions and sealing loading conditions. For delivery purposes, the stent-graft with a deployed outer diameter of 30 mm must first be shrunk to fit into the 24F delivery sheath and then, when deployed, must regain its original shape. The shrinking maneuver is modeled by applying a radial displacement to a rigid movable surface, which is in frictionless contact with the strut outer surface. The graft material has been assumed to have a negligible effect on the overall behavior of stent in the sealing section; thus the graft was not considered in the model. With respect to the sealing loading, the stent should be anchored to the neck artery of the abdominal aortic aneurism (AAA) after its release from the deployment system. The anchoring force should be sufficiently high to prevent the stent-graft migration. In this study, the stent deployment was modeled in two steps. First, the stent was shrunk to a diameter close to the artery interior wall by using rigid contact surface. Second, the stent expanded to reach an equilibrium radius in contact with the artery wall by gently removing the contact surface of the rigid body. The diastolic and systolic blood pressures were modeled as constant pressures applied to the inner surface of the artery wall.

Figure 5:
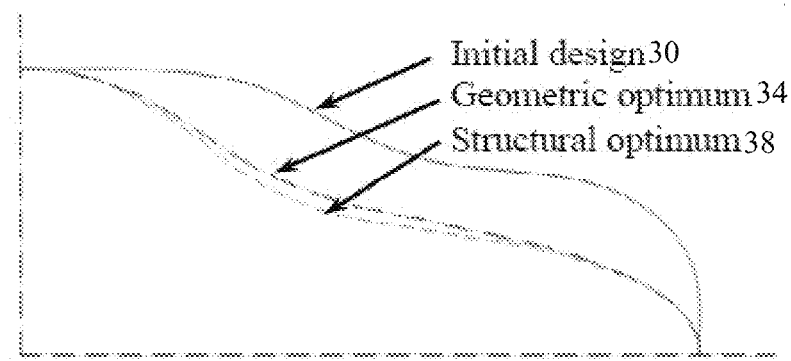
FIG. 5 illustrates exemplary geometric and structural optimized curves for a D stent lattice cell.
Figure 6:
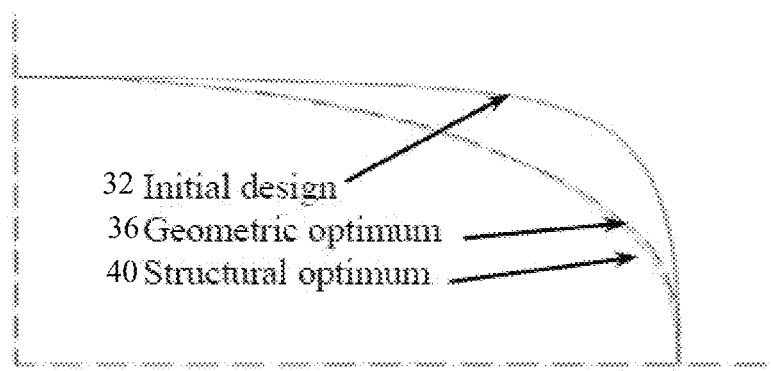
FIG. 6 illustrates exemplary geometric and structural optimized curves for an E stent lattice cell.

FIGS. 5 and 6 illustrate the results of minimizing the curvature of the inner boundary-profile for the D lattice cell and the E lattice cells, respectively. As described above, the initial geometric primitives 30 and 32 of the unit cell are $G^2$-continuous. The curves 34 and 36 represent the geometric optima obtained by minimizing the curvature while assuming constant weighting factors. The curves 38 and 40 are the structural optimum solutions obtained by iteratively minimizing the curvature with variable weighting factors, each updated according to equation (9) with respect to the FEA results. The structural optimization significantly changes the boundary-profile of the geometrically optimized D cell, whereas it has a negligible effect on the boundary-profile of the E cell.

Figure 7:
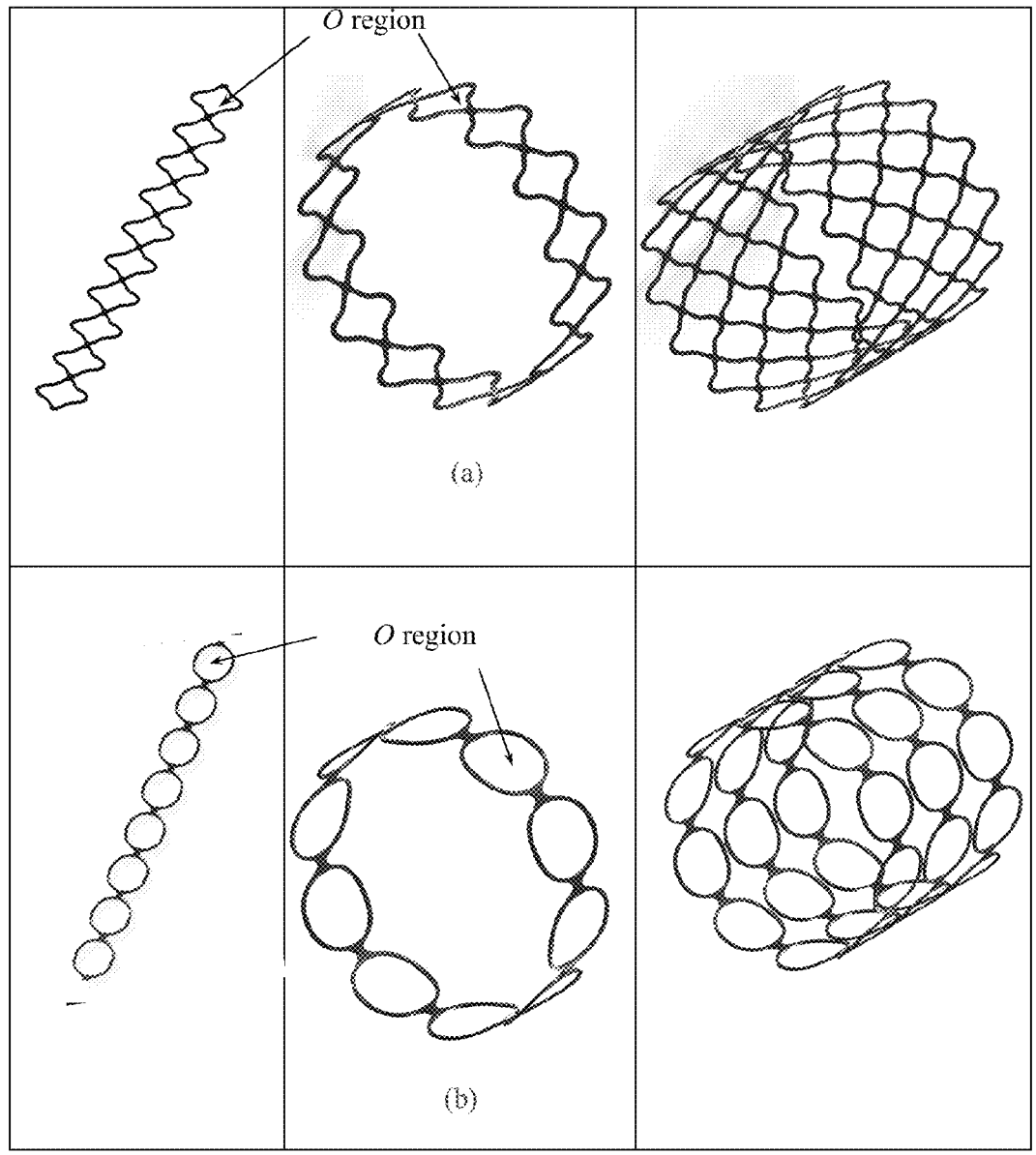
FIGS. 7a and 7b illustrate a straight row of cells, a cell row folded into cylinder, and an assembly of three folded rows of cells for a D geometry and an E geometry, respectively.
Figure 8:
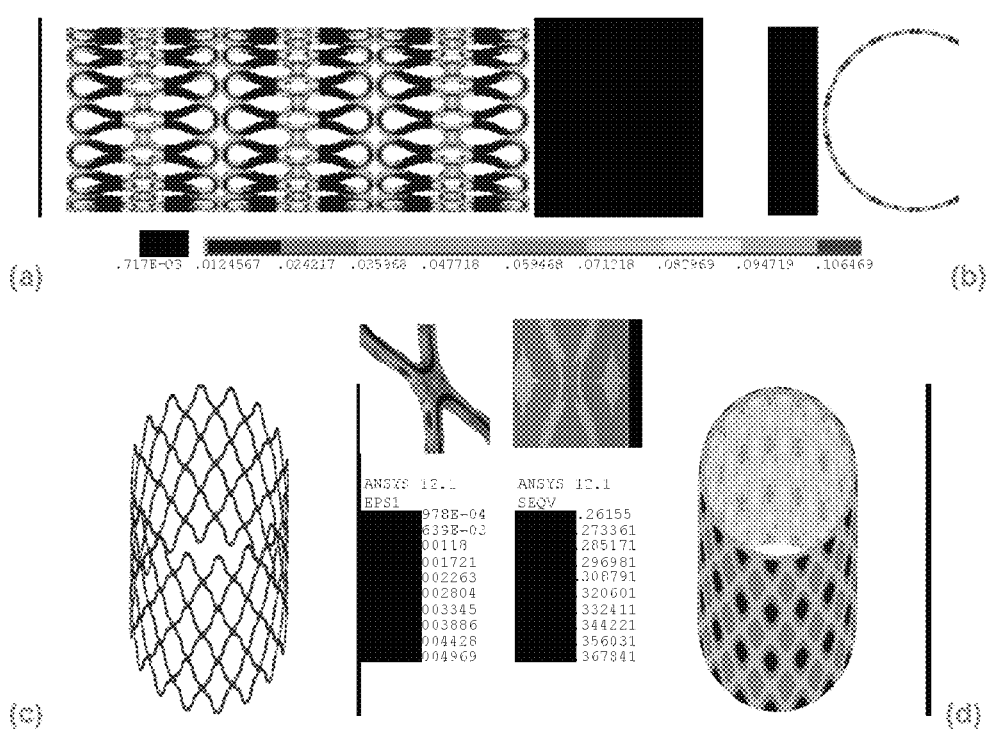
FIGS. 8a-8d illustrate exemplary stress distributions in a shrunk stent, first principal strain in a stent, and von Mises stress distribution in an artery after stent deployment under 100 mm-Hg mean pressure, for a D cell geometry.
Figure 9:
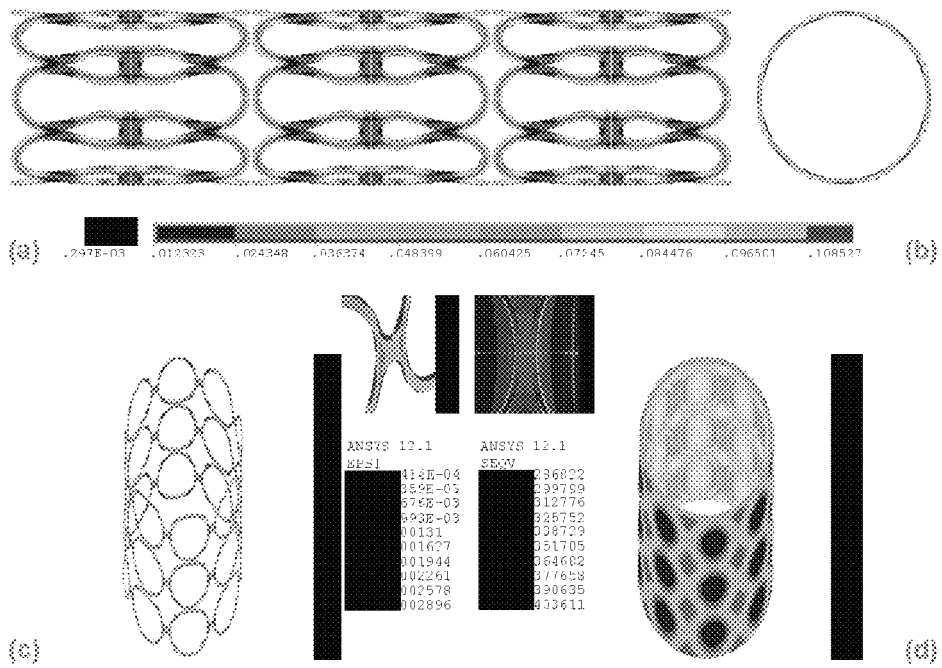
FIGS. 9a-9d illustrate exemplary stress distributions in a shrunk stent, first principal strain in a stent, and von Mises stress distribution in an artery after stent deployment under 100 mm-Hg mean pressure, for an E cell geometry.

FIGS. 7a and 7b illustrate a straight row of optimized cells, a row folded into cylinder, and an assembly of three folded rows of optimized cells for the D and E cell geometries, respectively.

TABLE 1

|  | Radial force at 100 mmHg (N) | Fatigue safety factor | Wall stress (MPa) | Maximum shrunk strain (%) |
| --- | --- | --- | --- | --- |
| D cell | 3.17 | 3.21 | 0.403 | 10.6 |
| E cell | 3.315 | 3.70 | 0.367 | 10.85 |
| R cell | 1.7 | 2.01 | 0.265 | 8.86 |

Figure 10:
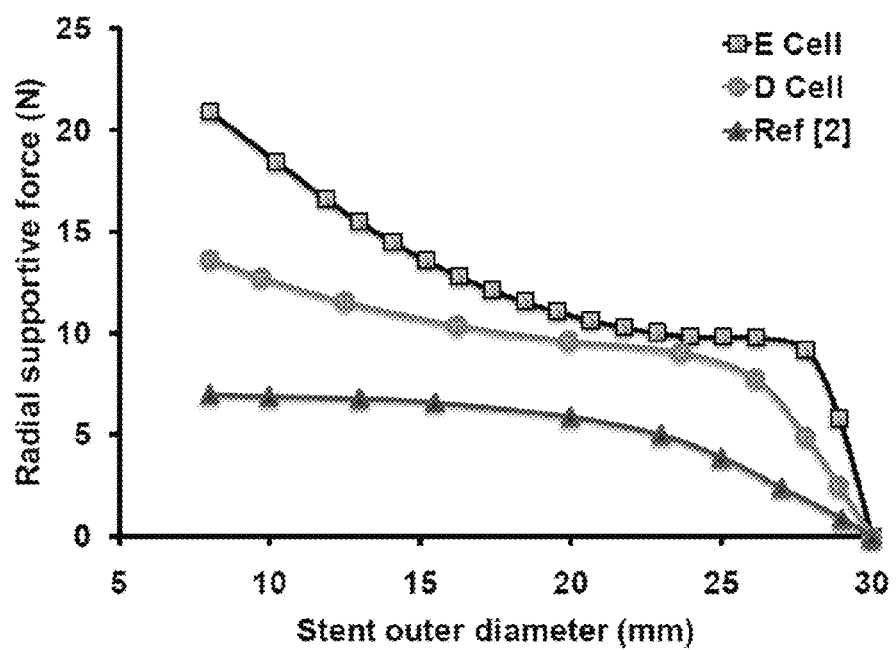
FIG. 10 illustrate an exemplary radial supportive force versus stent outer diameter of E, D, and R cell stents.

FIGS. 8a-b and 9a-b illustrate the von Mises strain distribution in the shrunk stent with E and D lattice cells. Since the maximum strain level in the shrunk lattice is below the 12% recoverable strain limit of Nitinol, the proposed cell geometries are fully deployable. The distribution of the first principal strain in the deployed D and E stents are illustrated in FIGS. 8c and 9c. Table 1 shows the performance of the proposed designs in comparison with an R stent design. The table shows that the proposed methodology for synthesizing stress concentration-free D (E) cell geometries enables to obtain stent lattices with 59.7% (84.3%) improvement in the fatigue safety factor and 87% (95%) increase in the radial supportive force per unit of stent area. FIGS. 8d and 9d illustrate the von Mises stress distribution induced in the artery wall after graft deployment. The stress level in the artery wall is below 0.67 MPa, the elastic limit of the artery. However, compared to the R stent, the level of von Mises stress induced in the artery wall by D(E) cell geometries exhibits a 38% (52%) increase. FIG. 10 illustrates the radial supportive force as a function of the outer diameter for E and D stents in comparison with the R stent for a prescribed stent area and tube thickness. For a 2 mm constant radial displacement, the proposed D (E) cell designs provide 82% (165%) increase in the supportive radial force.

To discuss the effect of the changes in the geometry of the optimized D and E stents, there was performed a parametric study that assessed the effect of $n_c$, $n_l$, t, and w on i) the deployed stent supportive radial force under 100 mmHg blood pressure; ii) stent fatigue safety factor; and iii) stent area. FIG. 11 summarizes the results. As can been seen, the application of the proposed methodology enables to find a lattice design with a higher fatigue safety factor and an improved radial supportive force. In particular, for a 25% increase of nc, nl, t, and w, the radial supportive force for D (E) cell enhances respectively by 2.3% (1.4%), 10% (18.55%), 16.9% (7.39%), and 7.91% (2.11%). The fatigue safety factor improves by 0.46% (49.7%), 64.13% (45.5%), 33% (50.7%), and 32.6% (41.6%). The stent area also increases by 19.1% (14.7%), 8.9% (14.8%), 21.4% (16.1%) and 0% (0%).

In one embodiment, the above benefits come along with a side-effect, i.e. an increase of the level of von Mises stress induced in the artery wall by 45% (36%) for D (E) cell. This is caused by the higher radial supportive force applied by the sharp edges of the stent struts in contact with the artery wall. Despite the stress increase in the artery wall, however, the contact stress distribution induced by D and E cells on the artery wall is more uniform. Furthermore, this stress level can be easily reduced by rounding the sharp fillet of the strut edges of the stent in contact with the artery.

The results of the parametric study show that to obtain a fully deployable stent an upper limit is required on the number of cells in the circumferential direction. For example, FIGS. 11a-11c show that for an E type stent with $n_l$=10, t=0.28 mm, w=0.45 mm, only values of $n_c$ less than 10 enable the stent to fully deploy.

Figure 11A:
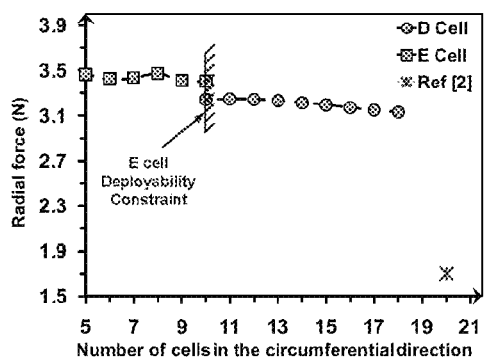
FIGS. 11a-11c exemplarily illustrate an effect of a number of cells in a circumferential direction of a stent on a radial force, a fatigue safety factor, and a stent area.
Figure 11B:
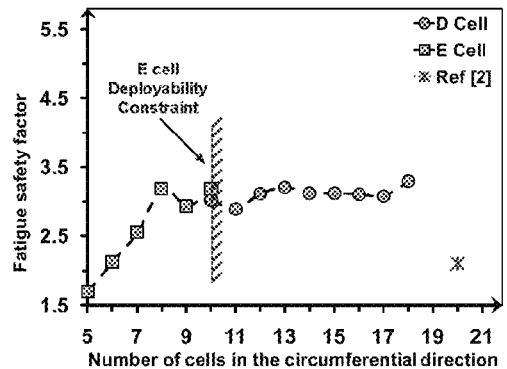
Figure 11C:
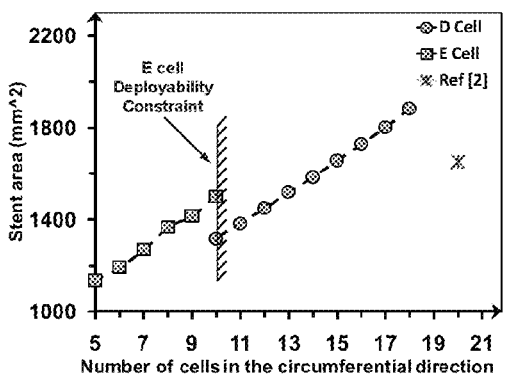

The impact of the number of cells in the circumferential direction, $n_c$ is illustrated in FIGS. 11a-11c. Whereas the supportive radial force of the stent is not affected, the stent area shows a rapid linear increase. For E stent, the fatigue safety factor, on the other hand, decreases if $n_c$ reduces, as opposed to D stent. Therefore, the D lattice should be preferred for smaller values of $n_c$, whereas higher values of $n_c$ should be chosen for the E lattice provided the deployment constraint is met (see FIG. 11a). However, reducing $n_c$ is not always beneficial. Rather, a low $n_c$ might have two effects. First, it might enhance the stress level in the artery wall. Second, it might increase the risk of the tissue to prolapse into the inner area of the lattice cell, illustrated in FIGS. 5 and 6 as the "O region".

Figure 11D:
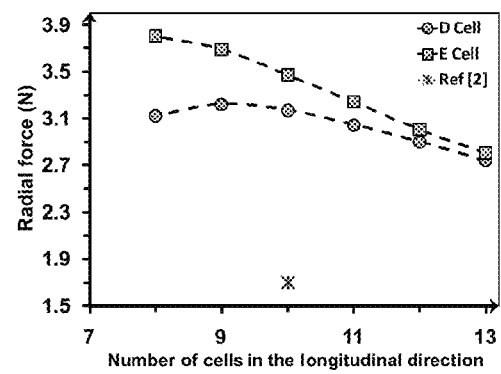
FIGS. 11d-11f exemplarily illustrate an effect of a number of cell rows in a longitudinal direction of a stent on a radial force, a fatigue safety factor, and a stent area.
Figure 11E:
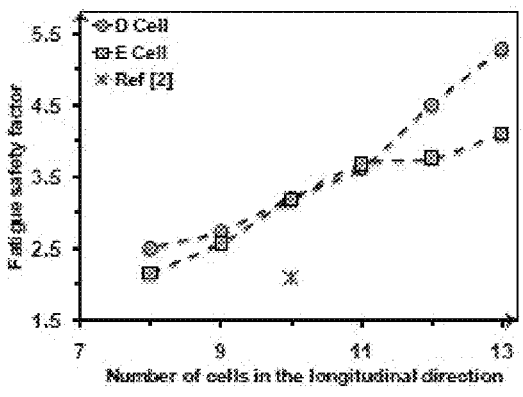
Figure 11F:
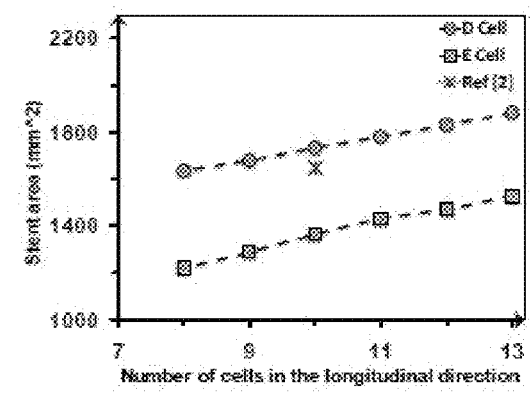

FIGS. 11d-11f illustrate the influence of the number of cells, $n_l$, in the longitudinal direction on radial force, fatigue life and stent area. An increase of $n_l$ results in a substantial reduction of the level of radial supportive force. This is because for a given arterial length, e.g. 100 mm, the radial force exerted on the artery is distributed more uniformly in stents with higher $n_l$; thus the involvement of a larger number of cell rows makes lower the share of the radial load. As a result, the stiffness of a stent increases if the length of each cell row is shortened, thereby reducing the amplitude of the alternating stress and improving fatigue life. Thus, the fatigue safety factor and the stent area increase proportionally with $n_l$.

Figure 11G:
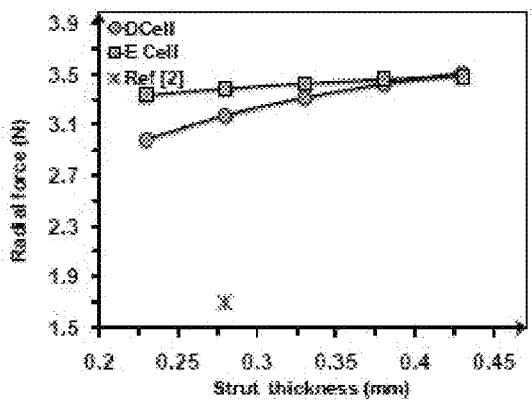
FIGS. 11g-11i exemplarily illustrate an effect of a stent thickness on a radial force, a fatigue safety factor, and a stent area.
Figure 11H:
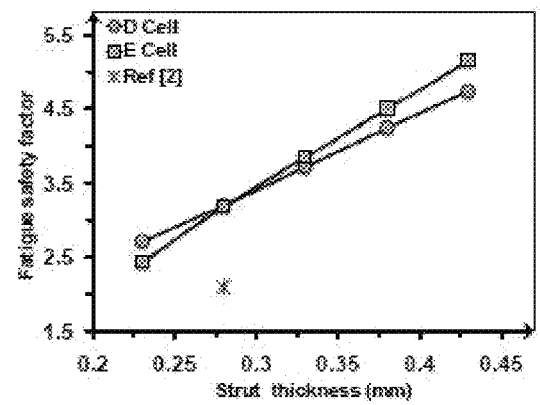
Figure 11I:
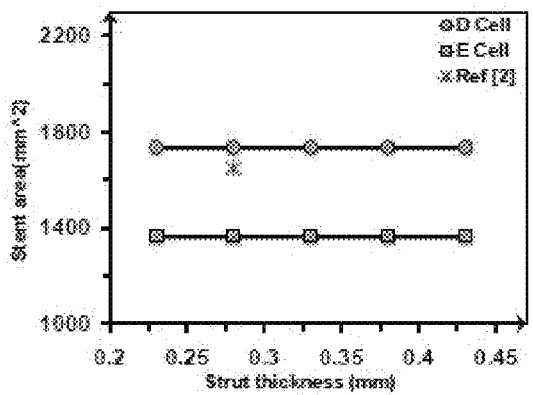
Figure 11J:
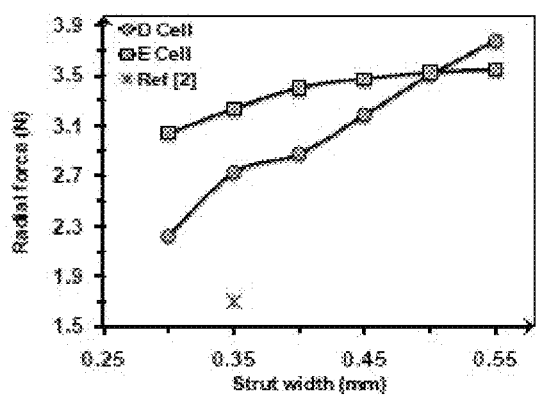
FIGS. 11j-11l exemplarily illustrate an effect of a strut width on a radial force, a fatigue safety factor, and a stent area.
Figure 11K:
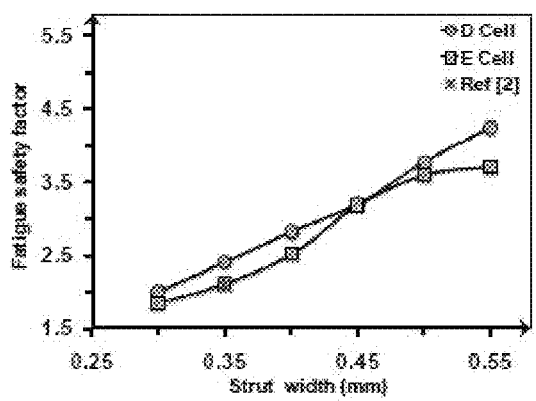
Figure 11L:
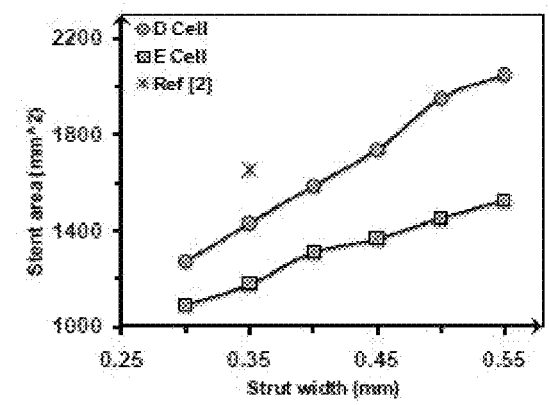

FIGS. 11g and 11j illustrate that thickening the strut thickness and width is beneficial for both stent radial stiffness and radial supportive force. Besides these gains, a stiffer stent would be also more resistant to the deformation imposed by a pulsatile pressure, thereby reducing the alternating strain experienced by its members. This is observed in FIGS. 11h and 11k, where the fatigue safety factor of both D and E lattices increases linearly with w and t. On the other hand, FIG. 11i shows that the stent area is not affected by any change of the stent thickness as opposed to the trend observed by varying $n_c$, $n_t$, w in FIGS. 11c, 11f, and 11l.

The result of FIG. 11g should, however, be taken with caution since both the artery contact stress and the role of blood flow play an important role. A thicker strut will cause a higher contact stress in the artery wall. Blood flow in proximity with the artery wall and the artery wall will affect the selection of the strut thickness. Both these issues should be determined through multi-disciplinary analysis and optimization involving both computational fluid dynamics and structural analysis.

Figure 12:
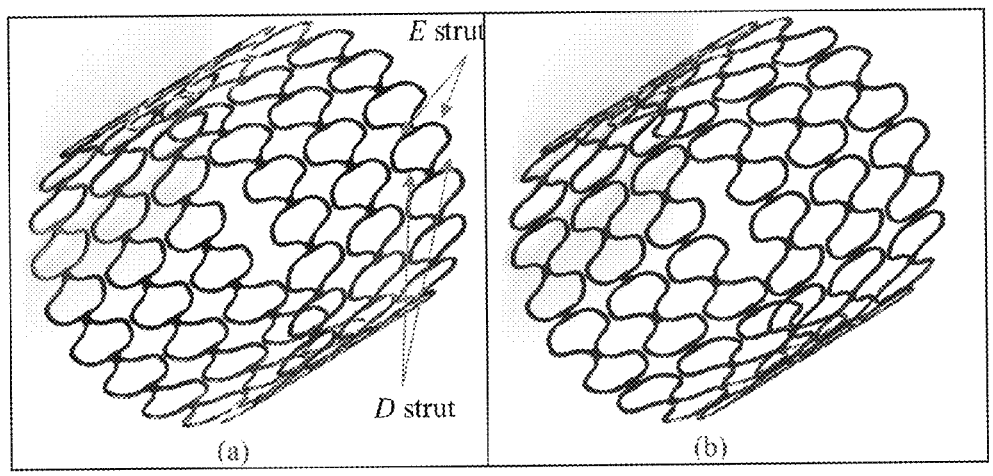
FIGS. 12a and 12b illustrate two hybrid designs for a stent, in accordance with an embodiment.

FIG. 11a-11g show that D and E cells are stiffer in the radial direction and have a higher fatigue life with respect to the reference stent design. Despite these advantages, a drawback of these cells is the risk of tissue prolapsing inside the artery wall. This phenomenon would occur in the "O region" depicted in FIG. 7 for D and E cells. These regions result from the selection of the cell shape besides from the fulfillment of the requirement for stent deployment, which imposes an upper limit on the maximum number of nc. In one embodiment, the problem of prolapsed tissue may be solved by combining the E and D cells into a hybrid cell shape. Two geometric primitives of the D cell are assembled with two of the E cell. FIGS. 12a and 12b show two possible variations of the hybrid stent design stemming from the E and D cell shape. Preliminary FEA results showed that these hybrid structures can fully resolve the drawback described above with only 6% reduction in the radial supportive force, and 4.5% reduction in the fatigue safety factor.

As shown by the results of this parametric study, stent radial supportive force, fatigue failure safety factor, and stress level in the artery wall may have conflicting outcomes. An improvement of one may penalize the other. It may, thus, be necessary to formulate the shape synthesis of the lattice cell within a multi-objective optimization framework, which would provide trade-off solutions among conflicting objective functions, such as those identified above.

As shown above, the present design methodology based on shape optimization improves the fatigue safety factor and increases the radial supportive force of Nitinol self-expandable stents with close cell geometry. To reduce abrupt changes of the cell geometry, the shape of the lattice cell has been synthesized with geometric primitives of continuous curvature. The bending moments caused by curved cell members are reduced by minimizing their curvature with the goal of making them as straight as possible.

The method has been applied to optimize the cell shape of a lattice Nitinol stent-graft. Two novel cell geometries have been synthesized; their radial supportive force and fatigue safety factor have been studied through a FEA parametric study. Compared to recent stent design, the results have shown an improvement of stent anchoring performance and a reduction of the risk of fatigue failure. The potential risk of prolapsed tissue has been identified and a solution of a hybrid design that combines the proposed lattice cells has been proposed. Further work is required to reduce the level of von Mises stress induced in the artery wall as well as to optimize simultaneously radial supportive force, fatigue safety factor and stress level of the artery wall.

Figure 13:
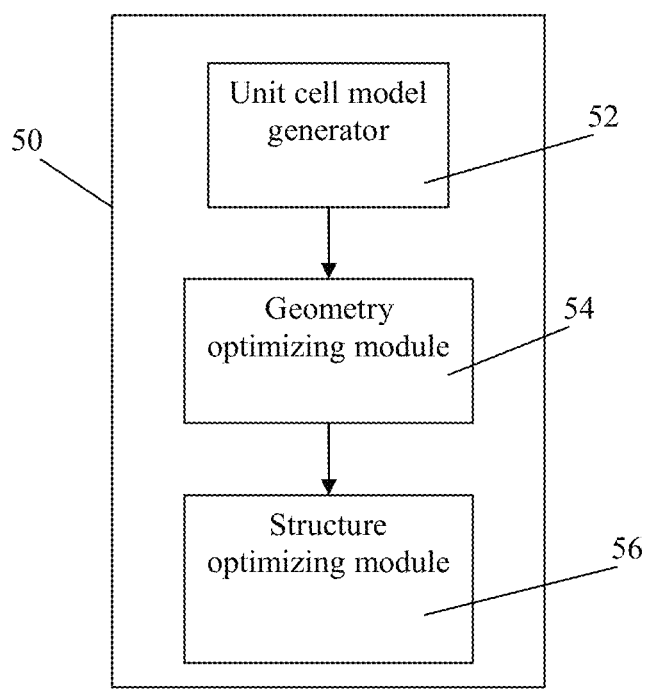
FIG. 13 is a block diagram of a system for designing a stent lattice cell, in accordance with an embodiment.

It should be understood that the above described methods may be embodied in different ways. For example, FIG. 13 illustrates one embodiment of a system 50 for generating the shape of a stent lattice cell. The system 50 comprises a unit cell generator 52 for generating a unit cell model representing a stent cell using the above described method, a geometry optimization module 54 for optimizing the geometry of the stent cell using the above described method, and a structural optimization module 56 for optimizing the structure of the geometrically optimizing stent cell using the above described method.

Figure 14:
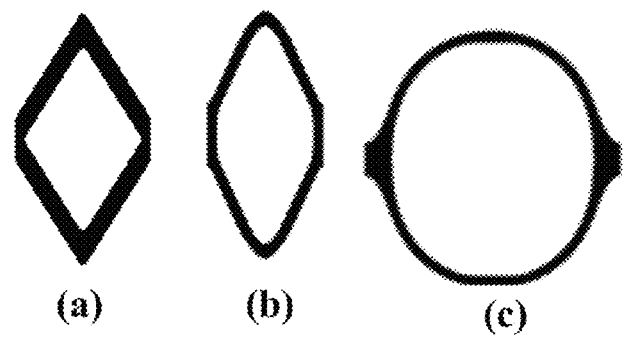
FIGS. 14a-14c illustrate three unit cells used to develop finite element models of abdominal aortic aneurism stent-grafts.

Referring to FIG. 14a, FIG. 14b, and FIG. 14c, finite element (FE) models of AAA stent-grafts with sharp-corner diamond (see FIG. 14a), rounded diamond (see FIG. 14b), and superellipse (see FIG. 14c) unit cells were developed. The rounded diamond and superellipse unit cells were optimized as described above, while the sharp-corner diamond unit cell was set as a benchmark. The FE models demonstrate that the proposed methodology for synthesizing a stress concentration-free cell with the superelliptical shape of FIG. 14c results in a 84.1% improvement in the fatigue safety factor and an 95% increase in the radial outward force per unit of stent area, as compared to the baseline sharp-corner diamond cell design of FIG. 14a. The FE models further demonstrate that using the rounded diamond shape of FIG. 14b results in a 26.4% improvement in the fatigue safety factor and a 60% increase in the radial outward force per unit of stent area, as compared to the baseline sharp-corner diamond cell design.

Figure 15:
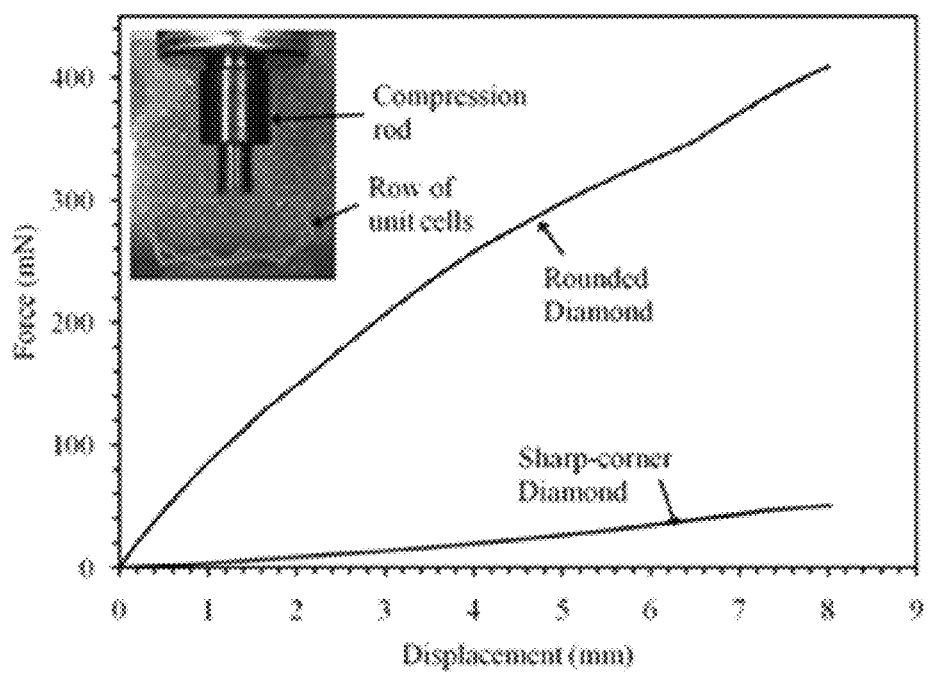
FIG. 15 illustrate an experimental test set-up and resulting radial compressive stress strain curves of two stent prototypes.

As seen in FIG. 15, the FE results pertaining to the radial outward force were qualitatively confirmed by compression testing, which was performed on sharp-corner and rounded diamond prototypes made of VeroWhitePlus™ resin by 3D printing. The FE models and mechanical testing results indicate that the fatigue life and stent fixation of the proposed designs are likely to outperform those of existing designs.

In one embodiment, the system 50 may be further configured for generating the shape of the whole stent. In this case, the system 50 further comprises a stent generator adapted to replicate the optimized stent cell output by the structural optimization module 56 to form a stent lattice and fold the stent lattice to form a substantially cylindrical 3D surface in order to obtain a stent structure which is output.

Figure 16:
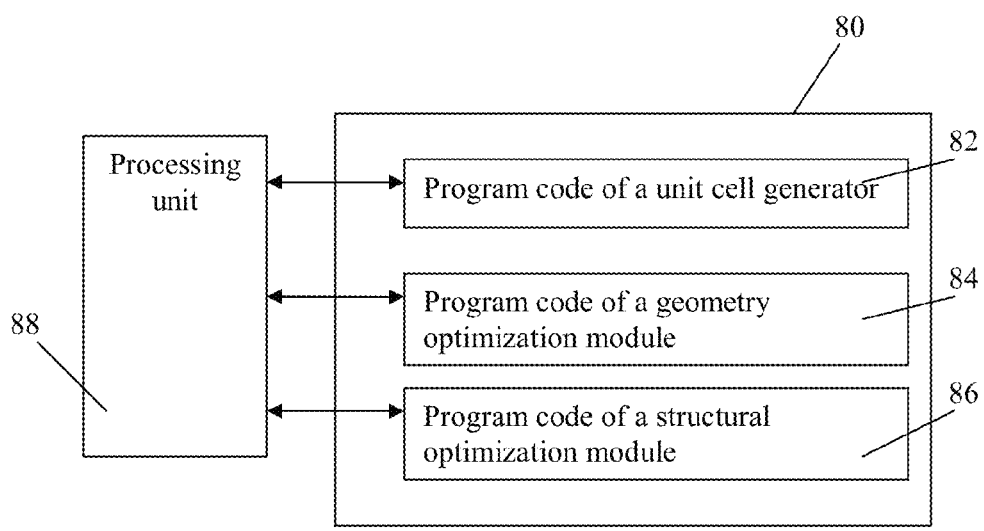
FIG. 16 is a block diagram of a memory having stored thereon program code for designing a stent lattice cell, in accordance with an embodiment.

The above described methods may also be embodied as software products stored on physical storage mediums. For example, FIG. 16 illustrates one embodiment of a memory 80 having stored therein program code 82 of a unit cell model generator for generating a unit cell model representing a stent cell using the above described method, program code 84 of a geometry optimization module for optimizing the geometry of the stent cell using the above described method, and program code 86 of a structural optimization module for optimizing the structure of the geometrically optimizing stent cell using the above described method. The program codes 82, 84, and 86 are to be executed by a processing unit 88 such as the processor of a computer for example.

In one embodiment, the memory 80 may further comprise program code of a stent generator (not shown) for replicating the optimized stent cell to form a stent lattice and fold the stent lattice to form a substantially cylindrical 3D surface in order to obtain a stent structure. The memory 80 may also have stored therein program code of a lattice geometry optimization unit (not shown) for finding the coating material thickness and profile optimum for maximizing the strength of the stent-coating interface. Using such a coating material, the risk of delamination or failure of the stent coating can be minimized.

While the invention has been described with particular reference to the illustrated embodiment, it will be understood that numerous modifications thereto will appear to those skilled in the art. Accordingly, the above description and accompanying drawings should be taken as illustrative of the invention and not in a limiting sense.

The above description is meant to be exemplary only, and one skilled in the art will recognize that changes may be made to the embodiments described without departing from the scope of the invention disclosed. For example, while generally described with respect to SE stents, which work in the elastic region of the stress-strain curve, it is to be understood that the present method and system can also be used for BE stents, however because BE stents work in the plastic region of the stress-strain curve, i.e. past the yield point, given that they require a balloon for deployment, the corresponding pertinent region of the stress-strain curve should be considered when calculating the weighting factors. Still other modifications which fall within the scope of the present invention will be apparent to those skilled in the art, in light of a review of this disclosure, and such modifications are intended to fall within the appended claims.

What is claimed is:

1. A method for generating a lattice cell shape for a stent made of a lattice of a given material comprising:
    generating a unit cell model representing the lattice cell, the unit cell model comprising a plurality of geometric primitives interconnected by blending points, each of the geometric primitives defining a G2-continuous curve at the blending points;
    setting a weighting factor to a same value for each one of the plurality of blending points, the weighting factor representing a contribution of a corresponding one of the plurality of blending points to a curvature of an optimal curve;
    determining a curvature of the G2-continuous curve as a function of the weighting factors having the same value; and
    structurally optimizing the unit cell model by iteratively and sequentially:
    determining a variable value for the weighting factor value for each one of the plurality of blending points, the variable value for the weighting factor value being calculated at each iteration using at least strain characteristics for the given material, determining a new curvature of the G2-continuous curve as a function of the variable value, and
    minimizing said new curvature, until obtaining an optimized curve corresponding to an optimized shape of the lattice cell; and
    generating the lattice cell shape for the stent having said optimized shape.

2. The method of claim 1, further comprising the step of optimizing a geometry of the unit cell model by minimizing the curvature of the G2-continuous curve, thereby obtaining an intermediate curve representing an intermediate unit cell model, and then performing the step of structurally optimizing on the intermediate unit cell model.

3. The method of claim 2, wherein the step of optimizing the geometry of the unit cell model comprises minimizing a root mean square value of a curvature of the geometric primitives defining the G2-continuous curve.

4. The method of claim 1, wherein the step of structurally optimizing the unit cell model comprises iteratively determining the variable value for the weighting factor value for each one of the plurality of blending points using strain characteristics for Nitinol.

5. A method of forming a stent of a given material with a lattice structure having a plurality of lattice cells, the method comprising:
    generating a unit cell model representing one of said lattice cells, the unit cell model comprising a plurality of geometric primitives each having a plurality of blending points interconnecting the geometric primitives and defining a G2-continuous curve;
    setting a weighting factor to a same value for each one of the plurality of blending points, the weighting factor representing a contribution of a corresponding one of the plurality of blending points to a curvature of an optimal curve;
    determining a curvature of the G2-continuous curve as a function of the weighting factors having the same value;
    structurally optimizing the unit cell model by iteratively determining a variable value for the weighting factor value for each one of the plurality of blending points, the variable value for the weighting factor value being calculated at each iteration using at least strain characteristics for the given material, determining a new curvature of the G2-continuous curve as a function of the variable value, and minimizing the new curvature, thereby obtaining an optimized curve corresponding to an optimized lattice cell shape;
    generating the lattice structure having the plurality of lattice cells each having said optimized lattice cell shape: and
    forming the stent by forming a 2D lattice structure using the lattice structure with the said optimized lattice cell shape and folding the lattice structure to form a tubular 3D lattice, thereby creating the stent.

6. The method of claim 5, further comprising the step of optimizing a geometry of the unit cell model by minimizing the curvature of the G2-continuous curve, thereby obtaining an intermediate curve representing an intermediate unit cell model, and then performing the step of structurally optimizing on the intermediate unit cell model.

7. The method of claim 6, wherein the step of optimizing the geometry of the unit cell model comprises minimizing a root mean square value of a curvature of the plurality of geometric primitives defining the G2-continuous curve.

8. The method of claim 5, wherein the step of structurally optimizing the unit cell model comprises iteratively determining the variable value for the weighting factor value for each one of the plurality of blending points using strain characteristics for Nitinol.

9. The method of claim 5, further comprising applying a coating material to the stent, the coating material having a predetermined thickness and profile and defining an interface between the stent and the coating material.

10. A stent comprising of a tubular lattice structure having a substantially cylindrical shape, the tubular lattice structure comprising a plurality of repeating lattice cells formed as defined in the method of claim 1.

11. A stent comprising of a tubular lattice structure having a substantially cylindrical shape, the tubular lattice structure comprising a plurality of repeating lattice cells formed as defined in the method of claim 5.

12. A system for generating a lattice cell shape for a stent comprising: a memory;
    a processor coupled to the memory; and
    program code stored in the memory and executable by the processor, the program code comprising:
    a unit cell generator for generating a unit cell model representing a stent cell to be made of a given material, the unit cell model comprising a plurality of geometric primitives each comprising a plurality of blending points defining a G2-continuous curve;

a structural optimization module for iteratively determining a variable value for a weighting coefficient for each one of the plurality of blending points, the variable value for the weighting factor value being calculated at each iteration using at least strain characteristics for the given material, the weighting coefficient representing a contribution of a corresponding one of the plurality of blending points to a curvature of an optimal curve, determining a curvature of the G2-continuous curve as a function of the variable value, and minimizing the curvature in order to obtain an optimized curve corresponding to an optimized stent cell shape; and a lattice cell shape generator for generating the lattice cell shape for the stent having the optimized stent cell shape.

13. The system of claim 12, further comprising a geometry optimization module for optimizing a geometry of the unit cell model by minimizing the curvature of the G2-continuous curve in order to obtain an intermediate curve representing an intermediate unit cell model, and using the intermediate curve in the structural optimization module.

14. The system of claim 13, wherein the geometry optimizing module optimizes the geometry of the unit cell model by minimizing a root mean square value of the curvature of the plurality of geometric primitives defining the G2-continuous curve.

15. The system of claim 12, wherein the structural optimization module iteratively determines the variable value for the weighting coefficient for each one of the plurality of blending points using strain characteristics for Nitinol.

16. A system for forming a stent lattice structure for a stent comprising: a memory;

a processor coupled to the memory; and program code stored in the memory and executable by the processor, the program code comprising:

a unit cell generator for generating a unit cell model representing a stent cell to be made of a given material, the unit cell model comprising a plurality of geometric primitives each comprising a plurality of blending points defining a G2-continuous curve;

a geometry optimization module for setting a weighting coefficient to a same value for each one of the plurality of blending points, the weighting factor representing a contribution of a corresponding one of the plurality of blending points to a curvature of an optimal curve, determining a curvature of the G2-continuous curve as a function of the weighting factors having the same value, and optimizing a geometry of the unit cell model by minimizing the curvature of the G2-continuous curve in order to obtain an intermediate curve representing an intermediate unit cell model;

a structural optimization module for iteratively determining a variable value for the weighting factor value for each one of the plurality of blending points, the variable value for the weighting factor value being calculated at each iteration using at least strain characteristics for the given material, determining a curvature of the intermediate curve as a function of the variable value, and minimizing the curvature in order to obtain an optimized curve corresponding to an optimized stent cell shape; and a stent generator which generates the optimized stent cell shape of the stent lattice and forms the stent lattice structure having said optimized stent cell shape.

17. The system of claim 16, wherein the geometry optimizing module optimizes the geometry of the unit cell model by minimizing a root mean square value of the curvature of the plurality of geometric primitives defining the G2-continuous curve.

18. The system of claim 16, wherein the structural optimization module iteratively determines the variable value for the weighting factor value for each one of the plurality of blending points using strain characteristics for Nitinol.

19. The system of claim 16, the program code further comprising a lattice geometry optimization module operable to select a thickness and profile of a coating material applied to the stent lattice structure.

20. A non-transient computer readable medium having stored thereon program code executable by a processor for generating a lattice cell shape for a stent, the program code comprising:

program code of a unit cell generator for generating a unit cell model representing a stent cell to be made of a given material, the unit cell model comprising a plurality of geometric primitives each comprising a plurality of blending points defining a G2-continuous curve;

program code of a geometry optimization module for setting a weighting coefficient to a same value for each one of the plurality of blending points, the weighting factor representing a contribution of a corresponding one of the plurality of blending points to a curvature of an optimal curve, determining a curvature of the G2-continuous curve as a function of the weighting factors having the same value, and minimizing the curvature of the G2-continuous curve, thereby obtaining an intermediate curve representing an intermediate unit cell model;

program code of a structure optimization module for iteratively determining a variable value for the weighting factor value for each one of the plurality of blending points, the variable value for the weighting factor value being calculated at each iteration using at least strain characteristics for the given material, determining a curvature of the intermediate curve as a function of the variable value, and minimizing the curvature, thereby obtaining an optimized curve corresponding to an optimized stent cell shape; and program code of a lattice cell shape generator for generating the lattice cell shape for the stent having the optimized stent cell shape.

21. The non-transient computer readable medium of claim 20, the program code further comprising a stent generator for replicating the optimized stent cell to form a stent lattice and folding the stent lattice to form a substantially cylindrical 3D surface in order to obtain a stent structure.

22. The non-transient computer readable medium of claim 21, the program code further comprising a lattice geometry optimization module operable to select a thickness and profile of a coating material applied to the stent structure.

* * * * *